United States Patent [19]

Hardway, Jr. et al.

[11] 4,033,332

[45] July 5, 1977

[54] ACTIVITY AND RESPIRATION MONITOR

[75] Inventors: Edward V. Hardway, Jr., Houston; William H. Holtman, LaPorte, both of Tex.

[73] Assignee: Cavitron Corporation, New York, N.Y.

[22] Filed: July 21, 1975

[21] Appl. No.: 597,726

Related U.S. Application Data

[62] Division of Ser. No. 287,844, Sept. 11, 1972, Pat. No. 3,926,177.

[52] U.S. Cl. .............................. 128/2 S; 324/61 R
[51] Int. Cl.² ............................................. A61B 5/10
[58] Field of Search ............. 128/2 R, 2 S, 2.06 B, 128/2.08, 2.1 R, 2.1 Z, DIG. 26; 340/279; 317/249 R; 324/61 R

[56] References Cited

UNITED STATES PATENTS

| | | | |
|---|---|---|---|
| 2,755,796 | 7/1956 | Boucke ................................ | 128/2 R |
| 2,907,320 | 10/1959 | DeWeese et al. ................... | 128/2 R |
| 3,316,902 | 5/1967 | Winchel et al. .................... | 128/2.1 R |
| 3,324,848 | 6/1967 | Domeier et al. ................... | 128/2.08 |
| 3,452,743 | 7/1969 | Rieke ................................. | 128/2.1 Z |
| 3,611,174 | 10/1971 | Day ................................... | 128/2.06 B |
| 3,760,794 | 9/1973 | Bashem ............................. | 128/2 R |
| 3,796,208 | 3/1974 | Bloice ................................ | 128/2 S |

*Primary Examiner*—William E. Kamm
*Attorney, Agent, or Firm*—Kenneth Olsen; Philip Sperber

[57] ABSTRACT

A contactless activity and respiration monitor is described which includes a resilient, capacitive pad, which may be a mattress, or a pad used with a mattress, having a capacitor therein responsive to the activity or respiration of a body lying on it. Electronic capacitance sensing circuitry is disclosed which provides an indication or alarm in the event of excessive activity or apnea, or low or high respiration rate. Readouts of respiration rate, and number of events of activity may also be provided. Circuits are disclosed for filtering out large static or relatively long term changes in the capacitance of the capacitive pad while maintaining the high sensitivity necessary to sense movements caused by respiration.

7 Claims, 13 Drawing Figures

Fig-13 FAST ZERO SWITCH

Fig-12

ACTIVITY AND RESPIRATION MONITOR

This application is a division of copending application Ser. No. 287,844, filed Sept. 11, 1972, now U.S. Pat. No. 3,926,177.

This invention relates to a contactless monitor or alarm responsive to a condition of the bodies of humans or animals. In one of its aspects it relates to a monitor or alarm that responds to activity of humans or animals, and in another aspect it relates to a monitor or alarm for hospital and home use, which responds to respiration and apnea with particular application to detecting apnea in small infants.

Respiration monitors are used in hospitals to signal a nurse when a human patient develops an abnormal breathing rate or has stopped breathing. For example, it is common for the breathing of premature infants to be monitored in hospitals because a frequent cause of death is apnea (cessation of voluntary breathing), which can usually be corrected by cutaneous stimulation. Also, recent investigations have indicated that yearly in the United States, from 10,000 to 25,000 infants in their first few months who appear, even to physicians, to be normal and healthy, die in their cribs from unexplained causes. Most of these deaths occur at home during periods of sleep and are unobserved. The disease is often called "the sudden infant death syndrome". Recent investigations have also indicated that monitoring and surveillance of infants and especially infants at risk during the critical first 6 months for apnea and abnormal activity (struggling) might save lives, or at least provide more information concerning the cause of death. However, no suitable device has been provided for home monitoring of infant breathing functions or activity. Those generally used in hospitals would be impractical and dangerous for home use.

Some contactless monitoring devices are presently used in scientific research with non-human animals for studying the effects of various drugs, etc., on animal activity generally more rigorous than breathing. In the case where only gross activity of the human or non-human animal is being monitored, as opposed to breathing functions, the prior art has provided various devices using radio frequency or photo-electric signals to record activities which represent fairly large movements of the animal. However, these devices are generally not sensitive enough to also respond selectively to very small movements such as breathing or to the cessation of breathing, particularly where the patient monitored is a small infant.

To obtain the required sensitivity and reliability, the most commonly used prior apnea (and associated breathing) monitors are impedance plethysmographs requiring the patient to be wired with at least two electrodes installed on the chest. Other similar devices are also provided which require the patient to be wired. These devices are all cumbersome and the electrodes coming loose is a troublesome problem. These devices are also obviously undesirable for use as a home monitor since the requirement for attaching wires to the baby and the dangers of strangulation would probably make it unattractive to most mothers.

Several attempts have been made to provide contactless monitors for monitoring breathing and apnea, particularly for infants. One such device is a segmental air filled mattress in which very small volumes of air move from one inflated chamber in the mattress to another through a common manifold in response to movement of the mattress caused by breathing. The manifold contains an electrical airflow sensor. However, this device is cumbersome and capable of being deflated by a safety pin and is not suitable for home use. It is also subject to false alarms as its operation is dependent on the infant's location on the mattress. Another contactless monitor presently available has a small, thin transducer considerably smaller than the mattress of an incubator. The transducer is placed under the mattress to respond to motion caused by breathing of the baby. However, this transducer must be placed directly under the baby and if the baby moves away from the transducer it is possible that the loss of signal will be so great that the device would not indicate apnea. To reduce this problem, it would be necessary to increase its sensitivity to such a value that it would be subject to failure to detect apnea from any slight movement of the incubator — a failure that could cost the infant its life.

In monitoring breathing and loss of it, very small, short term motions are involved whereas normal activity, such as when the baby shifts its weight, provides motion of much greater magnitude. Sustained activity may indicate struggling because of inability of the baby to breathe. A difficult problem in the design of any apnea or breathing monitor is to reduce the possibility of false alarms and compensate for the larger or longer term motions in a manner to insure that the smaller motions are reliably detected and that cessation of the smaller motions is detected so that an apnea alarm is given only when apnea occurs. Failure to meet these conditions may destroy the confidence of the nurse or mother attending the infant in the reliability of the alarm device, which can be a very dangerous circumstance.

It is thus an object of this invention to provide a contactless activity and respiration monitor, for responding to and distinguishing between small movements of the body of a subject being monitored due to breathing, including apnea, and larger movements of the body, with greater reliability and fewer false alarms than prior such devices.

Another object of this invention is to provide such a monitor which detects and provides an alarm when apnea occurs for longer than a preselected period of time, or when respiratory rate falls either above or below a present level (or both).

Another object of this invention is to provide such a monitor in which a capacitive, non-pressurized incubator or crib mattress or pad is used which has substantially equal levels of sensitivity to motion over the entire upper surface.

Another object of this invention is to provide such a monitor which may be used to detect and provide an alarm when activity amplitudes of the body of the subject being monitored continues to exceed one or more given levels as would be the case if an infant were struggling for breath.

Another object of this invention is to provide such a monitor which may be used as an activity monitor which records or counts activity of a subject (particularly small animals) exceeding one or more given levels as events per unit time.

Another object of this invention is to provide a monitor such as described which may be suitable for home use for monitoring of small infants.

These and other objects of this invention, which will be apparent upon consideration of the appended claims and drawings, and the following detailed description of this invention, are accomplished according to the embodiments illustrated by providing a variable capacitance or capacitive pad substantially the same size as a mattress or other pad on which the subject to be monitored is lying (or the mattress or other pad may be the sensing pad) so that a given movement of the subject from breathing or other activity at substantially any place on the mattress or pad will cause a detectable and substantially equal change in the capacitance of the sensing pad. An electronic capacitance sensing circuit is connected to the capacitive pad and responds to any change in capacitance to provide an electrical signal which may be used to detect activity or apnea and provide an alarm if a signal does not occur within a preselected period of time, i.e. 10-20 seconds, or if any other abnormal condition occurs. Circuits are provided which permit the apparatus to automatically respond to long term capacitance changes, for example the shift in weight of the subject, and to restore the baseline level to zero without appreciably affecting the sensitivity of the apparatus. The circuits act as first order or single pole high pass (for example, breathing frequency) filters. A fast zero switch may also be provided to shorten the response time of such circuits during very large capacitance changes.

In the drawings, wherein preferred embodiments of this invention are shown and like reference numerals are used throughout to designate like parts.

Figure 1:
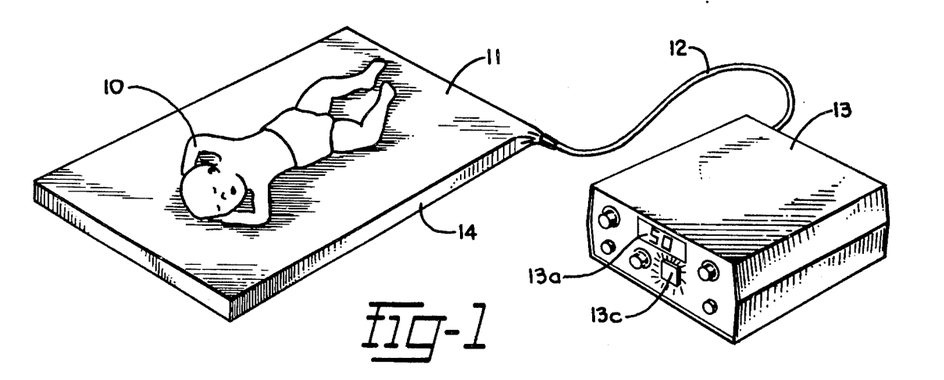
FIG. 1 is a perspective view of the capacitive pad of this invention and shown with the alarm unit containing the electronic sensing circuits connected to it.

Referring now to the drawings, FIG. 1 shows infant 10 lying on a capacitive pad 11 which may be a mattress or mattress pad connected by shielded cabling 12 to an electronic alarm unit 13. Alarm unit 13, which includes the electronic sensing circuitry of this invention, may include a digital readout 13a (which may also be an analog readout) of respiration rate, and a visual alarm 13c for indicating apnea or excessive activity. An audio alarm (at the rear of the case and not shown) sounds an audible alarm when apnea occurs for longer than a preset time interval.

It is to be understood that capacitive pad 11 may be either a complete mattress, such as when a permanent installation in a hospital incubator is provided with the electrodes of this invention installed in it, or may just be a pad with the electrodes in it which can be placed under or on top of a regular mattress and is substantially the same size of the mattress, such as would be provided with a home monitor. Also, where animal activity is monitored it may be a pad in the bottom of the cage. Reference herein to pad or capacitive pad is intended to refer to both the integral capacitive mattress and the separate capacitive pad configuration.

Figure 2:
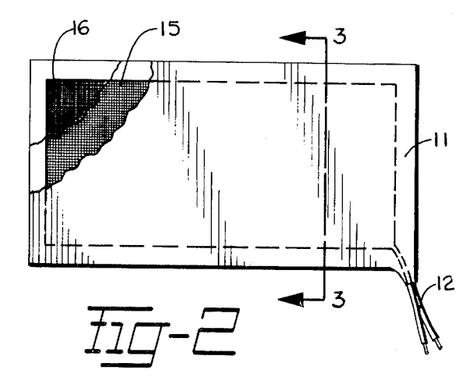
FIG. 2 is a top view in elevation of the capacitive pad of FIG. 1.
Figure 3:
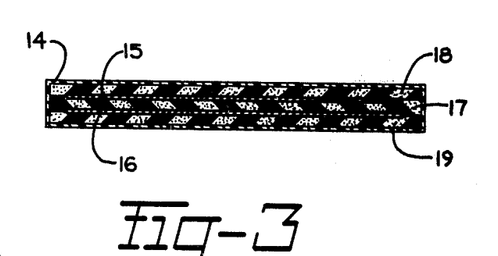
FIG. 3 is a cross section view taken at 3—3 in FIG. 2.

One version of such a pad is shown in FIGS. 2 and 3. In this version, when using a D.C. source to excite pad 11, the entire pad may be shielded from stray power line pickup by conductive plastic 14 connected to the shield of cable 12. An outer layer of insulation (not shown) between the top of covering 14 and baby 10, should be used if the shield is connected to a ground common to the power line ground.

As shown in FIG. 3, pad 11 has two thin metal or fine conductive wire mesh electrodes 15 and 16, separated from each other by a layer 17 of resilient polyurethane foam or other elastomer foam, and from the top of pad 11 by a foam or other elastomer layer 18, and the bottom of pad 11 by a foam or other elastomer layer 19. It is preferable to have layer 19 denser than layers 17 and 18 for maximum sensitivity.

Figure 4:
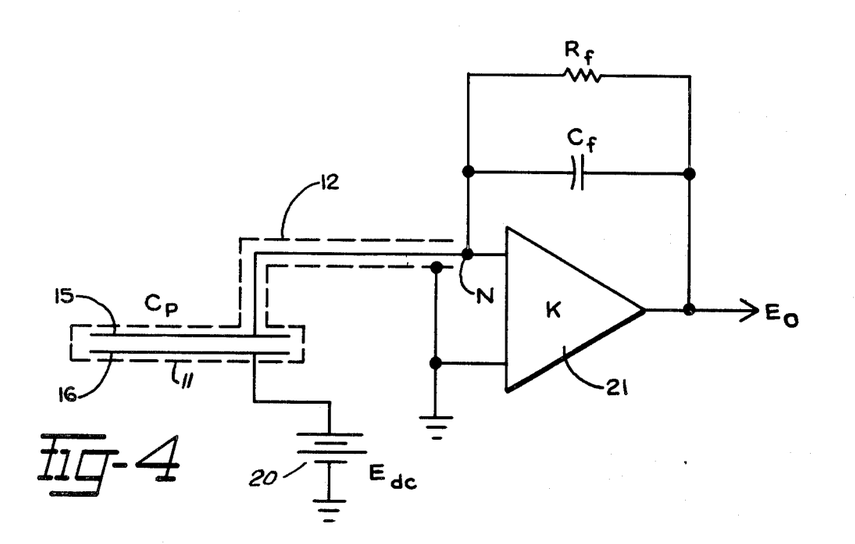
FIG. 4 is a schematic diagram of an equivalent circuit of the capacitive pad of FIG. 1 with a D.C. drive shown to the pad and the input amplifier of the electronic sensing circuit shown.

As shown in FIG. 4, electrode 15 and 16 cover substantially the entire area of pad 11 and form capacitive plates. Electrode 16 is connected to a source 20 of low level D.C. voltage $E_{dc}$ and a charge amplifier 21 having a feedback capacitance $C_f$, a feedback resistor $R_f$ and a gain of K is connected at its input through cable 12 to electrode 15. The input of amplifier 21 functions as a null junction N. The output of amplifier 21 is labeled as a voltage $E_o$ and will be responsive to the change in capacitance between electrodes 15 and 16 as the breathing of the baby causes movement of one of the electrodes with respect to the other.

Assume that a sleeping but breathing body such as baby 10 rests on pad 11 and that with the body weight in place the capacitance between electrodes 15 and 16 is:

$$C_p = C_{po} + C_{pb} + C_R \sin Wt \quad (1)$$

where:

$C_p$ = instantaneous capacitance
$C_{po}$ = capacitance with nothing on the pad
$C_{pb}$ = static change in $C_p$ caused by body weight
$C_R$ = amplitude of capacitance change caused by respiration (here assumed sinusoidal)
$W$ = frequency angular of occurrence of output signal $E_o$ which is generally the angular frequency of respiration with a sleeping baby.

Also by definition:

$$Q = E_{dc} C_p \quad (2)$$

and $i_1$, the current flowing into the null junction N is:

$$i_1 = dQ/dt = E_{dc}\, dC_R/dt = W\, C_R \cos Wt \quad (3)$$

Now the same current must flow from the output to the null junction. Therefore:

$$i_2 = E_o/R_f + C_f \, dE_o/dt = E_{dc} \, W \, C_R \cos Wt \qquad (4)$$

$$dE_o/dt + 1/R_f C_f \, E_o = E_{dc} \, W \, C_R/C_f \cos Wt \qquad (5)$$

The solution of the first order differential equation is:

$$E_o = E_{dc} \frac{C_R}{C_f} \frac{\sin(Wt - \phi)}{\sqrt{1 + \frac{1}{(WR_f C_f)^2}}} \qquad (6)$$

where $$\phi = \tan^{-1}(-1/WR_f C_f) \qquad (7)$$

Assuming that $R_f = \infty$; then $$E_o = E_{dc} \, C_R C_f \sin Wt \qquad (8)$$

It has been found experimentally using a pad with ⅜ inch thick foam between the electrodes, that a practical minimum figure for $C_R$ is 0.001pF, whereas $C_{po}$ may be of the order of 100pF. It is also known that a minimum acceptable breathing rate for infants is about 20 breaths per minute or 0.333 breaths per second. If a low frequency break point is chosen to be the same as $W_1$ so that the amplitude will be down approximately 30% at the lowest rate, $W_1$, then:

$$W_1 R_f C_f = 1 \qquad (9)$$

$$R_f C_f = 1/W_1 = 1/2\pi(0.333) = 0.478 \qquad (10)$$

and $$R_f C_f \cong 0.5 \qquad (11)$$

Thus, if $C_f$ were selected at 1000pF then $R_f = 500$ megohms. The amplitude of $E_o$ with $E_{dc} = 100$ volts would be:

$$E_o = 100 \, .001/1000 \, 1/\sqrt{2 \times 10^6} = 70 \text{ microvolts} \qquad (12)$$

This signal is sufficiently large to easily distinguish it from noise and use it in subsequent amplification.

Figure 5:
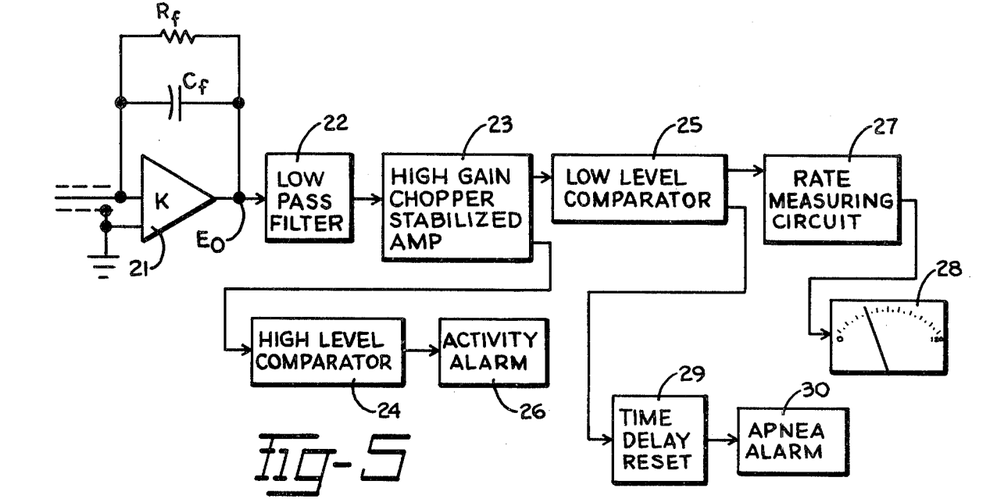
FIG. 5 is a block diagram showing one form of D.C. sensing circuitry that may be connected to the output of the amplifier in FIG. 4.

FIG. 5 is a block diagram showing how the output $E_o$ of charge amplifier 21 would be used in a general purpose respiration monitor. The output of amplifier 21 which serves as its own high pass filter with a cut-off frequency $f_{co}$ is fed into low pass filter 22, which may be cut off typically at 2 cps. The filter output goes to a very high gain chopper stabilized amplifier 23 which may have a gain ranging from $10^4$ to $10^5$. The amplifier 23 output goes to a high level comparator 24 and a low level comparator 25.

Comparator 24 senses large motions, i.e., greater than those caused by respiration indicating activity. Single activity or prolonged activity signals from comparator 24 actuates an activity alarm 26, which may be a visual indication or an audio alarm. The low level comparator 25 senses respiration and produces at least one pulse for each act of respiration. Comparator 25 output goes to a rate measuring circuit 27 which produces a current or voltage substantially proportional to rate which actuates a meter or display 28 (i.e. an analog equivalent to digital display 13a in monitor 13).

The output of comparator 25 also is connected to a time delay reset 29 which has a preset selectable time delay of, for example, between 10 and 20 seconds. Failure of a pulse to appear from comparator 25 within the preset time delay period causes the reset 29 to actuate an apnea alarm 30, which again may be an audio or visual alarm, or both.

If desired, rate circuit 27 may be connected to high or low rate alarms, and the output of the high limit comparator 24 may be recorded or counted to determine frequency of activity over long periods.

The above described embodiment of FIGS. 2–5, using a D.C. drive voltage $E_{dc}$ while similar in some respects to the A.C. embodiment of this invention to be described, are less preferred because of the requirement for complete shielding of the outer surface of the capacitive pad and the internal circuits from electrostatic pickup at power line frequency. Also, it would respond to electrostatic charges generated by motion of the cabling to the pad unless special non-microphonic cabling were used. However, it is believed that the above description of the FIGS. 2–5 embodiment will provide an understanding of the principles of this invention as they are applicable to the construction of pad 11, and to the utilization of the output signals obtained from the pad.

Figure 6:
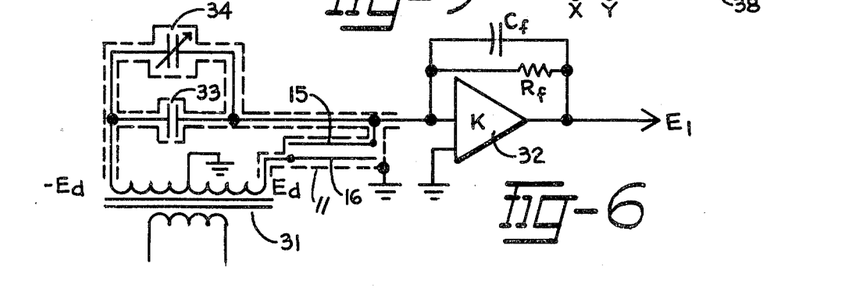
FIG. 6 is another equivalent circuit for the pad of FIG. 1 with an A.C. drive signal shown and the input amplifier for the electronic sensing circuitry shown.

In FIG. 6, an A.C. version of the monitor of this invention is shown in which the driven electrode 16 of pad 11 is connected to one side of the secondary of a drive transformer 31, and receptor electrode 15 is connected to an A.C. charge amplifier 32. Transformer 31 provides drive voltages $E_d$ and $-E_d$ of the same amplitude but opposite phase. External fixed capacitors 33 and 34, one of which may be variable, are connected to the other side of the secondary of transformer 31 to balance out the gross static capacitance between electrodes 15 and 16. The output $E_1$ of amplifier 32 may be connected for utilization to circuitry such as shown in FIGS. 10–13 and to be described. By use of the charge amplifier such as shown in FIGS. 4 and 6, a low impedance output connection for pad 11 is provided which minimizes the effect of stray and cable capacitance.

Figures 7, 8, 9:
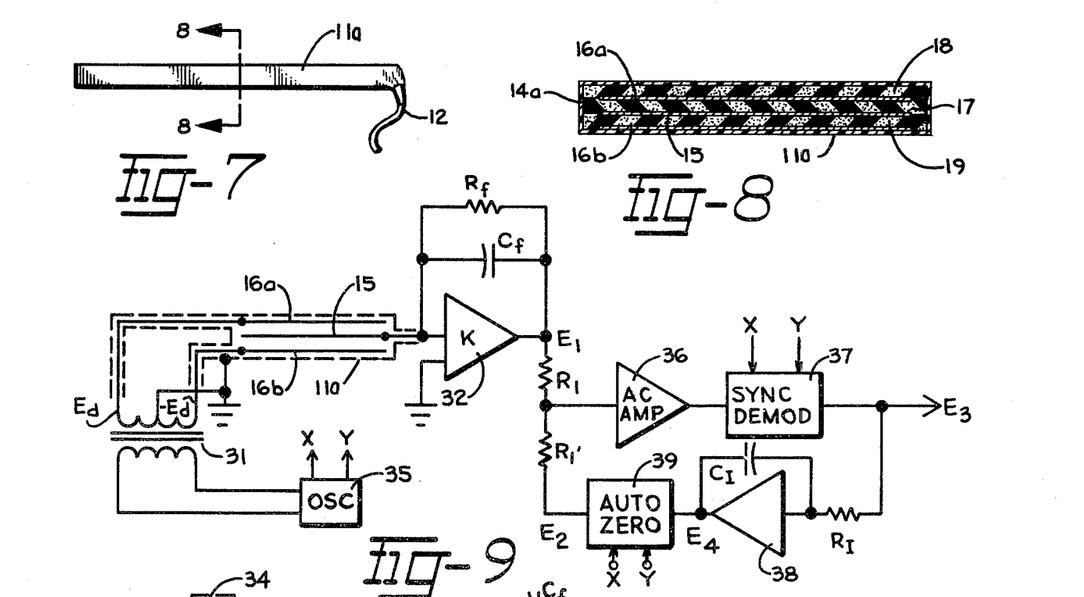
FIG. 7 is a side view in elevation of another form of sensing pad of this invention, which is preferred.
FIG. 8 is a cross section taken at 8—8 in FIG. 6.
FIG. 9 is an equivalent circuit of the pad of FIG. 7 with an A.C. drive signal and with a basic block diagram of an electronic sensing circuit for the pad shown.

In FIGS. 7 and 8 an alternate and in some applications a preferred form of pad 11 is shown which also may be used with an A.C. capacitance sensing circuitry such as shown in FIGS. 9 and 10–13.

In FIGS. 7 and 8, pad 11a is divided into three layers of foamed material, with a top layer 18, bottom layer 19, and intermediate layer 17, and includes a receptor electrode 15 between layers 17 and 19, a first driven electrode 16a between layers 18 and 17, and a second driven electrode 16b below layer 19 and between that layer and a conductive or non-conductive plastic cover 14a which encloses pad 11A. A conductive cover may be used for shielding although this is not necessary in this embodiment if adequate high pass filtering is used. Electrodes 15, 16a and 16b are preferably flexible wire mesh having substantially the same length and width as pad 11a. However, if desired, the electrodes may be made of a conductive plastic sheeting or a multiplicity of thin metal plates connected by fine wires so that each plate moves independently. It is important that the electrodes be sufficiently flexible and resilient to move with small movements of the pad over a large centrally located area of substantially all of the top surface area of the pad. Foam layer 19 is preferably more dense and stiffer than foam layers 17 and 18. When a breathing infant or other subject is lying on pad 11a or when pad 11 is under crib or incubator mattress, the relative motion between electrodes 15 and 16a as caused by breathing causes a change in capacitance which is substantially larger than the change in capacitance which would occur between electrodes 15 and 16b, further from the infant and separated by less resilient foam. However, with the arrangement of pad 11a in FIGS. 7 and 8, with two driven electrodes, a partial cancellation of static changes due to different body weight of the subject being monitored, would be provided.

FIG. 9 shows the basic block diagram of the front end of the A.C. sensing circuitry utilized with pad 11a shown schematically. Driven electrodes 16a and 16b are connected to opposite sides of the secondary of a drive transformer 31 providing A.C. drive voltages $E_d$ and $-E_d$ of the same amplitude, but opposite phase, typically 10–25 volts at 50KHz, and driven by an oscillator 35. The 50KHz drive signals serve as a carrier signal. Receptor electrode 15 is connected to the input of a charge amplifier 32 of gain K which provides an output signal $E_1$ proportional to capacitance changes between the electrodes 15 and 16a, and 15 and 16b, which, when equal, will be cancelled out. The definitions of capacitance are essentially the same as used in Equation (1) above except that they are differential quantities (indicated by a prime). $C_{\nu o}'$ is the static capacitive imbalance which could be close to zero.

The output $E_1$ of the charge amplifier 32 is given by:

$$E_1 = (C_\nu'/C_f) E_d \qquad (13)$$

and the ratio $K_o$ of the signal levels at the input and output of charge amplifier 32 is defined by:

$$K_o = E_1/C_\nu' = E_d/C_f \qquad (14)$$

Output signal $E_1$ is coupled through a resistor $R_1$ to an A.C. amplifier 36 which is connected to a synchronous demodulator 37 to provide a D.C. output signal $E_3$. Output signal $E_3$ is coupled through a resistor $R_I$ to an integrator circuit 38 which has an integrating capacitor $C_I$ and integrates voltage $E_3$ to produce a voltage $E_4$ which is the input voltage to an auto-zero circuit 39. Auto zero circuit 39 produces an A.C. output voltage $E_2$ synchronized with oscillator 35 and opposite in phase to $E_1$, which is conducted through a resistor $R_1'$ to the input of A.C. amplifier 36. Output voltage $E_3$ may also be coupled to output and utilization circuitry such as provided in the monitor of FIG. 10.

Auto zero 39 functions as a synchronous modulator generating the signal voltage $E_2$ to cancel long term changes in capacitance between electrodes 15, 16a and 16b, and allow only short term changes to appear as output voltages $E_3$. How this works will become evident from the equations below where $R_1 = R_1'$ and $K_1 =$ the ratio of the voltage levels $(E_1-E_2)/E_3$, $K_2$ is the ratio of the angular voltage levels $E_2$ and $E_4$, $W$ is the frequency of the occurrence of signal $E_1$ which, with a sleeping infant would generally be $W_R$ the angular frequency of respiration of the baby; and $T_I$ is the time constant of integrator 38 equal to $R_I C_I$:

$$K_2 = E_2 (A.C.)/E_4 (D.C.) \qquad (15)$$

$$E_3 = K_1 (E_1-E_2) \qquad (16)$$

$$E_4 = 1/R_I C_I \int E_3 dt \qquad (17)$$

$$E_4 = E_3/jWR_I C_I = E_3/jWT_I \qquad (18)$$

From equations 15, 16, and 18:

$$E_3 = \frac{K_1 E_1}{1 + \frac{K_1 K_2}{jWT_I}} \qquad (19)$$

$j$ is the imaginary operator $\sqrt{-1}$.

It is evident that all very slow changes in capacitance are balanced out when $W$ is very small or zero. In the absence of movement, the integrator 35 will continue to integrate $E_3$ causing an increase or decrease of $E_2$ until $E_2 = E_1$ and $E_3=0$. When an infant is placed on pad 11a, the effect of $C_{\nu o}'$ and $C_{\nu b}'$ are balanced out. Likewise a shift in weight of the infant is balanced out, but continued body movements are not. Thus, respiration, (assumed to be sinusoidal) will come through as:

$$E_1 = K_o C_R' \sin Wt \qquad (20)$$

After all static imbalances are cancelled. Hence:

$$E_3 = \frac{K_o K_1 C_R}{\sqrt{1 + \left(\frac{K_1 K_2}{WT_I}\right)^2}} \sin (Wt - \phi) \qquad (21)$$

The auto zero range must be sufficient to cancel any static imbalance i.e., $$E_2 (MAX) > K_0(C_{\nu o}' + C_{\nu b}')$$

Thus, the loop formed by circuit components 36, 37, 38, and 39 provide the function of high level signal amplification and detection while functioning as an electronic high pass filter for rejecting the relatively long term capacitance changes.

The similarity between the solution of the equations relating to the D.C. and A.C. embodiments described is significant dynamically, i.e. both the D.C. and A.C. versions include at least one single pole high pass electronic filter to reject or balance out static or long term changes of capacitance thousands of times larger than the changes that must be detected. However, for a practical activity and apnea monitor, it is preferred that the A.C. approach be used because:

a. The drive signal, for example at 50 KHz, is non-hazardous at reasonable voltage levels.

b. A.C. amplifier 36 (which may be several in series) are always operated within their range at balance, because of the auto-zero 39.

c. The great separation between the frequency of the 50 KHz drive signal and power line frequency of 50 or 60 Hz, (approximately 10 octaves) makes it easier to reject stray pickup without having to completely shield the pad.

By conducting output signal $E_3$ through an appropriate low pass filter, noise frequencies out of the breathing range can also be attenuated or substantially rejected.

Typical numbers used in apparatus used to date and employing the basic configuration of the figure of circuitry of FIG. 9 are:

$K_o = 0.25$ volts per picofarad
$K_1 = 225$
$K_2 = 0.1$
$R_I = 10$ meg.
$C_I = 2$ Mfd $T_I = 20$ sec.

The effective time constant of the auto-zero loop (i.e. the time required for a correction to be 63% completed) is:

$$T_{eff} + T_I/K_1K_2 = 20.0/22.5 = 0.89 \text{ Sec.} \quad (23)$$

The shorter $T_{eff}$ the faster the recovery from a change in static imbalance, however, the longer $T_{eff}$ the less attenuation of output $E_3$ at breathing frequencies. At 20 breaths per minute or 0.33 breaths per second the attenuation factor of A with the numbers used in the above example is:

$$\frac{1}{A} = \frac{1}{\sqrt{1 + \left[\frac{1}{.89(.33)(2\pi)}\right]^2}} = 0.88$$

Thus, by use of the auto-zero the baseline or zero level of signal $E_3$ can be automatically adjusted to a new level when a relatively long term capacitance change (i.e. about 1 sec. or longer) between the electrodes of pad 11a occurs.

Figure 10:
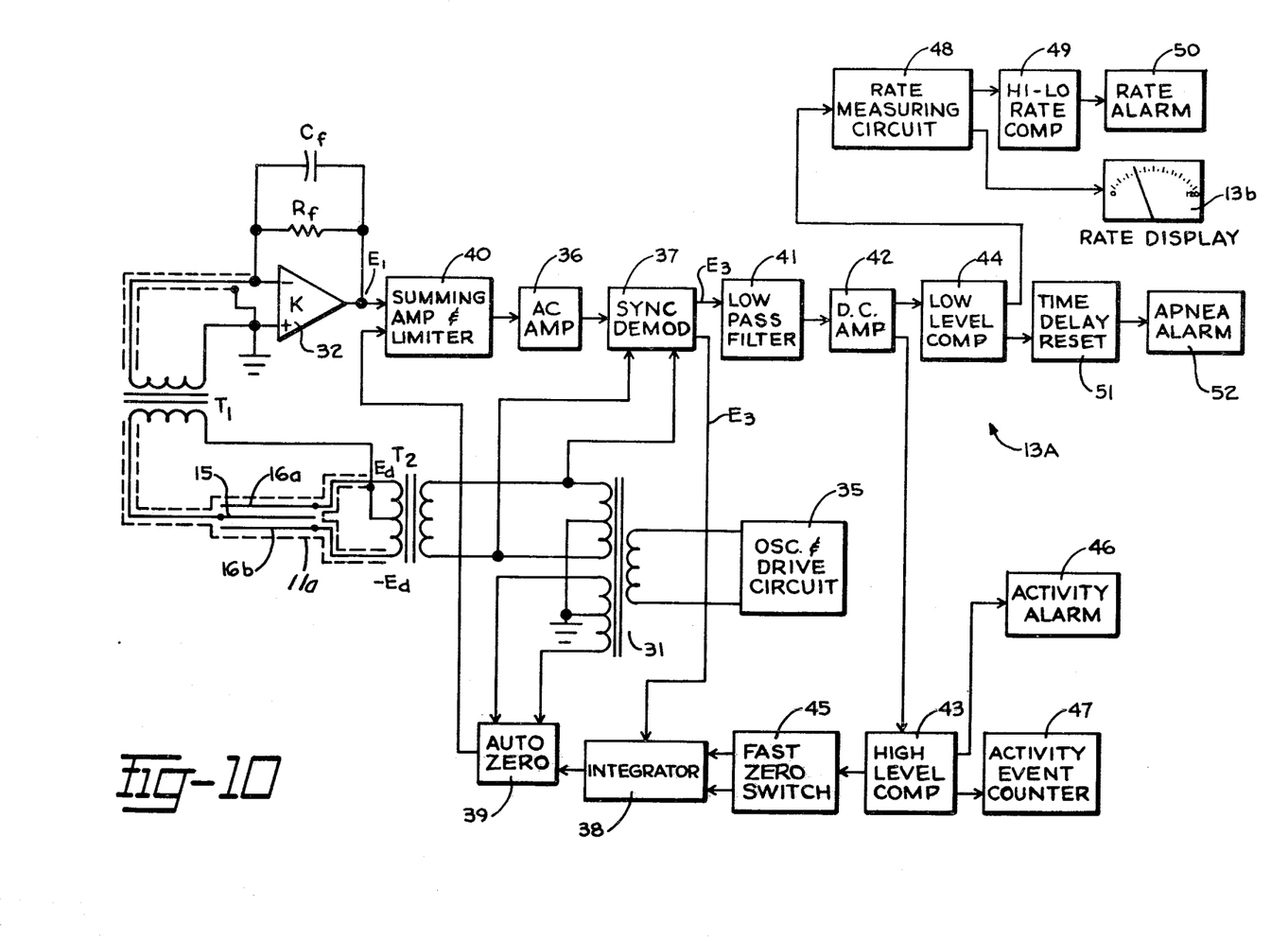
FIG. 10 is an overall block diagram of a respiration rate, activity, and apnea monitor using the principles of this invention.

Referring now to FIGS. 10–13, a preferred form of activity and apnea monitor 13A similar to monitor 13 is shown, except that the respiration rate display is shown as an analog readout instead of the digital readout shown by the number 50 in a window 13a in FIG. 1. Also, an optional activity event counter is provided which is not shown in monitor 13 of FIG. 1. In FIG. 10, pad 11a, shown schematically, may be any of the embodiments described, but the embodiment of FIGS. 7 and 8 is illustrated in conjunction with the circuitry of FIG. 10. The monitor of FIGS. 10–13 thus would be suitable for detecting and indicating apnea, rate of breathing and activity, and providing an alarm in the event of apnea and excessive activity, of human and non-human animals in the home, hospitals, or scientific laboratories.

As shown in FIG. 10, (the same reference numerals being used to identify components already described with respect to FIG. 9) drive transformer 31 is connected through isolation transformers $T_1$ and $T_2$ which are preferably provided for 50 Hz isolation and patient safety. The output $E_1$ of charge amplifier 32 is fed to a summing amplifier and limiter 40 which functions as did resistors $R_1$ and $R_1'$ in FIG. 9 to sum the outputs $E_1$ of charge amplifier 32 and $E_2$ of auto-zero circuit 39, and to also keep relatively large and long term capacitance offsets created by patient body movements on the pad from saturating the circuitry and rendering the monitor inoperative. The limiter section of amplifier 40 keeps A.C. amplifier 36 from completely saturating allowing auto-zero circuit 39 to operate faster and keep the A.C. signal at the output of amplifier 36 in proper phase for detection by synchronous demodulator 37. The output of summing amplifier and limiter 40 is conducted to the input of high gain A.C. amplifier 36 where it is amplified to a usable level and then conducted to the input of synchronous demodultor 37. Synchronous demodulator 37, which is synchronized with drive signals $E_d$ and $-E_d$ as shown, detects only signals in proper phase and rejects noise, and provides a D.C. output $E_3$ which is then conducted to a low pass filter 41 which filters out the noise that was not rejected by synchronous demodulator 37. Output $E_3$ of synchronous demodulator 37 is also fed to integrator 38 and auto-zero circuit 39, which as noted, corrects for long term capacitance changes at the input to charge amplifier 32 by feeding back an A.C. signal equal in amplitude and opposite in phase as the signal created by the long term capacitance change at the output of amplifier 32. This feedback signal is summed with the input signal at summing amplifier 40 which returns the D.C. output of synchronous demodulator 37 to zero at a slow rate, to provide a new baseline.

The D.C. signal at the output of low pass filter 41 is conducted to a D.C. amplifier 42 where it is amplified for signal processing. The output of D.C. amplifier 42 is then fed to a high level comparator 43 and a low level comparator 44, both of which may be ordinary voltage level comparators which provide an output when the input voltage level exceeds a preset threshold level. A very low frequency high pass filter (not shown) may be used following the D.C. amplifier to eliminate any problem with D.C. offset due to bias currents. High level comparator 43 may be set to respond to signal levels that are 10 times greater than the breathing signal, and which may be classified as signals representative of activity (other than breathing) of the subject being monitored. The output of high level comparator 43 which is a low level (i.e. zero volts) when the input from amplifier 42 is above the threshold level, and is at a high level (i.e. 5 volts) when the input level is below the threshold level, is conducted to a fast zero switch 45, an activity alarm 46 and an activity event counter 47. Activity alarm 46 can be a flashing light or an audible alarm, and activity event counter 47 is a counter that counts and stores each event classified as activity. Fast zero switch 45 is turned on each time the output of the high level comparator goes low and is connected to integrator circuit 38 in a manner to reduce the integrator time constant 38 and thus cause the D.C. output $E_3$ of synchronous demodulator 37 to return to zero volts sooner. The threshold of low level comparator 44 is set to detect smaller changes of capacitance at the input of charge amplifier 32 than comparator 43, and to classify these events as breaths. The output of the low level comparator 44 is conducted to a breathing rate measuring circuit 48 and a time delay reset circuit 51 which resets a preselected time delay with each output signal from the low level comparator 44. Should the time delay not be reset for a preselected time ranging from 10–20 seconds, the time delay reset circuit 51 output changes state and is conducted to an apnea alarm 52. The apnea alarm 52 can be a flashing light or an audible signal or both, each indicating that cessation of breathing has occurred. The breathing rate measuring circuit 48 which measures the breathing rate and feeds a D.C. output proportional to the rate to a display of an analog meter 13b, or to an analog to digital convertr (not shown) for driving digital readout such as 13a, shown in FIG. 1. This D.C. signal is also fed to a high-low breathing rate comparator 49 which gives an output if the breathing rate goes above or below a preset rate. The output from the breathing rate comparator 49 is then conducted to a rate alarm 50 which can be a flashing light (such as light 13c in FIG. 1) or an audible alarm. For example, in monitor 13 in FIG. 1 light alarm 13c may be used for both the breathing rate alarm and activity alarm 46.

Figures 11, 13:
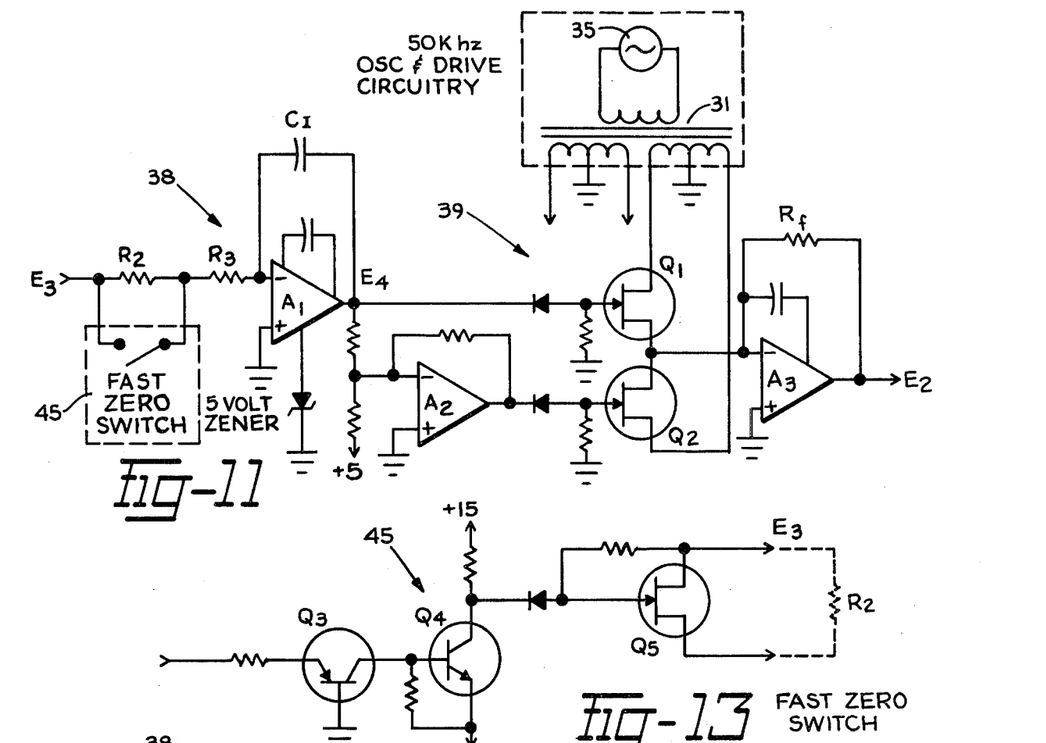
FIG. 11 is a detailed schematic diagram of one form of integrator and auto zero circuit that may be used with the monitor of FIG. 10.
FIG. 13 is a detailed schematic diagram of one form of a fast zero switch circuit that may be used with the monitor of FIG. 10.
Figure 12:
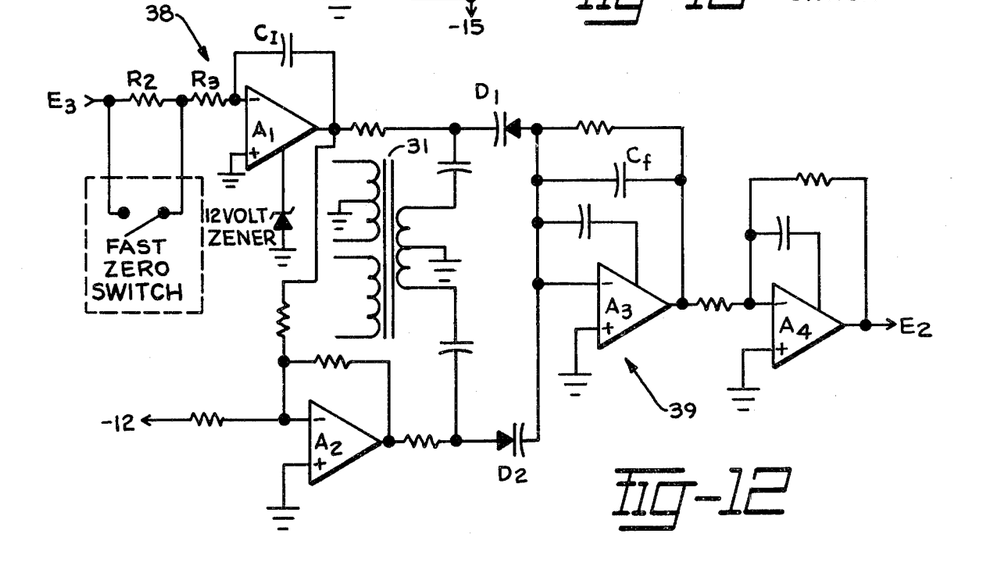
FIG. 12 is a detailed schematic of another form of an integrator and auto zero circuit that may be used with the monitor of FIG. 10.

The integrator circuit 38 and the auto-zero circuit 39 function as previously described and may take a number of different forms to provide a mechanical or electronic cancelling of long term capacitance changes. Preferred circuits for auto-zero 39 and integrator 38 are shown in FIG. 11 and less preferred circuits are shown in FIG. 12. Also, fast zero switch 45 may be a mechanical or electrical switch that functions as described, and a preferred form of such a switch is shown in FIG. 13.

Referring to the FIG. 11 embodiment of auto-zero circuit 39 and integrator circuit 38, an amplifier $A_1$ is connected as a pure integrator having a feedback capacitor with a capacitance of $C_I$, and functions as the error amplifier for the auto-zero circuit. The D.C. output $E_3$ of synchronous demodulator 37 is conducted to the input of amplifier $A_1$ which has zero volts or ground for its reference, through series resistors $R_2$ and $R_3$. The integration time constant of amplifier $A_1$ is determined by the product of input resistors $(R_2 + R_3) \times C_I$. Amplifier $A_2$ is a summing amplifier and level shifter which provides one-half of a differential drive to the gate electrodes of two field effect transistors $Q_1$ and $Q_2$. As the output of amplifier $A_1$ goes more positive, the output of amplifier $A_2$ goes more negative. The differential output voltages provided by amplifiers $A_1$ and $A_2$ are conducted to the gate electrodes of FETS $Q_1$ and $Q_2$ which function as variable impedance devices. The inputs of FETS $Q_1$ and $Q_2$ are connected to drive transformer 31 and thus are 50 KHz sinewaves that are equal im amplitude, but opposite in phase. The outputs of FETS $Q_1$ and $Q_2$ are connected together and summed at the input of an amplifier $A_3$, and then amplified by amplifier $A_3$ to provide feedback voltage $E_2$. The gain of $A_3$, and thus the signal level of the feedback voltage $E_2$, is determined by a feedback resistor $R_f$ connected from its output to its input, and the impedance of FETS $Q_1$ and $Q_2$ which varies as a function of the D.C. voltage levels at their gate electrodes. The output $E_2$ of amplifier $A_3$ will change amplitude and phase as the differential D.C. voltage applied to the gate electrodes of FETS $Q_1$ and $Q_2$ goes from one extreme to the other. The output $E_2$ of $A_3$ is fed back to the input of summing amplifier 40 and summed with the output $E_1$ of the charge amplifier to cancel this signal out and maintain the baseline ($E_3$) at zero volts, D.C.

Thus, with the integration time constant correctly chosen, short term capacitance changes, such as from breathing, will result in signals at the output of the synchronous demodulator 37 above and below a baseline of substantially zero voltage level. Under these conditions, the input to and the output from amplifier $A_3$ will remain constant. When a long term capacitance change occurs (i.e., longer than the time constant determined by $(R_2 + R_3) \times (C_1)$ such as when an infant is shifted in position on the pad 11, amplifier $A_3$ will slowly change and provide a different level of output voltage $E_2$ for cancelling the long term or average value of voltage $E_1$ from charge amplifier 32 of FIG. 10.

Another version of an auto-zero circuit 39 is shown in FIG. 12. This circuit is the same as shown in FIG. 11 except that it uses varactor diodes $D_1$ and $D_2$ as the variable elements in the feedback loop. The capacitance from anode to cathode of the varactors changes as the D.C. bias voltage across the diode is varied. Amplifier $A_1$ again is connected as a pure integrator and functions as the error amplifier for the auto-zero circuit. The D.C. output $E_3$ of synchronous demodulator 37 is fed to the input of amplifier $A_1$ which is again referenced to zero volts, through series input resistors $R_2$ and $R_3$. The integration time constant is again determined by the product of $(R_2 + R_3) \times C_I$. Amplifier $A_2$ is a summing amplifier and level shifter which provides one-half of the differential D.C. bias voltage to $D_1$ and $D_2$. $D_1$ and $D_2$ are driven with 50 KHz sinewaves from drive transformer 31 that are equal in amplitude and opposite in phase. The output of $D_1$ and $D_2$ is summed at the input of charge amplifier $A_3$ and its output is then amplified to a usable level $E_2$ and fed to the capacitance measuring circuit at the input of amplifier 40 in FIG. 10 where it is summed with the output $E_1$ of the input charge amplifier. As the input voltage $E_3$ to $A_1$ goes above or below 0 volts, the D.C. bias voltage across $D_1$ and $D_2$ varies to provide the necessary amplitude and phase to correct for the change in capacitance at the input of the capacitance measuring circuit, in the same manner as described with respect to the FIG. 11 embodiment.

In both FIGS. 11 and 12, fast zero circuit 45 is illustrated as a mechanical switch shunting input resistor $R_2$ to reduce the integration time constant of integrator 38 whenever voltage $E_3$ exceeds a preset high level. As shown in FIG. 13 a preferred form of this switch includes transistors $Q_3$ and $Q_4$ and a field effect transistor $Q_5$ that exhibits a very high impedance when turned off and a low impedance when turned on. The output of high level comparator 43 which for example may be at a five (5) volts positive, is conducted to transistor $Q_3$. Transistors $Q_3$ and $Q_4$ are normally conducting keeping the gate of the FET $Q_5$ at about negative fifteen (15) volts which keeps it turned off. When the baseline voltage $E_3$ exceeds the preset high level, the high level comparator trips and its output goes to zero volts turning off transistors $Q_3$ and $Q_4$. This turns on the field effect transistor $Q_5$ and shunts $R_2$ with a low impedance to reduce the integrator time constant. $Q_5$ remains on until $E_3$ returns to a preset low level when high level comparator 43 goes back to a positive 5 volts turning on transistors $Q_3$ and $Q_4$ and turning off FET $Q_5$.

In the circuits of this invention shown, the input amplifier is shown as a charge amplifier i.e. with a capacitor in the feedback loop clamping the receptor electrode of the pad at virtual ground. The charge amplifier with the D.C. feedback resistor $R_f$ serves as a high pass filter. In the A.C. circuits $R_f$ has no function except to stabilize the input amplifier, but the charge amplifier with capacitor $C_f$ provides power amplification of the high frequency signal with minimal phase shift and makes the three-terminal capacitive measurement substantially independent of cable length. However, any suitable input amplifier may be used if all other functional circuit requirements are met in the alternate circuit.

The measurement of capacitance may be made between one electrode in the pad and a grounded, driven or receptor electrode beneath the mattress without departing from the spirit of this invention. Basically, this invention is concerned with a resilient mattress or pad with at least one flexible electrode extending over a substantial portion (i.e. the part that the baby is likely to be over) of the mattress surface area, so that a capacitance change occurs when the mattress surface is depressed.

Essential to operation of the invention is a high pass electronic filter with time constant $R_f C_f$ in FIG. 4 and $R_f C_I / K_1 K_2$ in the A.C. version and wherein the time constant is long enough to allow passage of signals occuring at the breathing or activity frequencies being detected. In the AC version an auto-zero circuit is used (which may be any suitable working embodiment of a synchronous modulator or analog multiplier which instantaneously multiplies the 50 KHZ signal by the integrator output) to provide a long term balancing signal $E_2$, the latter being the product of one phase of the reference 50 KHZ carrier voltage and the integrator output voltage $E_4$. In FIG. 9, the product $E_1R_1$ is used to cancel long term changes at the output of the amplifier 32, and, of course, cancellation could also be effected at the input of amplifier 32.

Thus, as can be appreciated from the above description, pad 11 and monitor 13 can provide surveillance of a subject, such as an infant, without any need for wiring the subject, and with complete safety to the subject. The monitor would be equally suitable for use in a hospital, home or a scientific or medical laboratory. Either cessation of respiration, (apnea) or struggling activity such as would occur when an infant is attempting to regain its breath, would initiate an alarm and provide an opportunity for corrective measures to be taken.

From the foregoing, it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth (or shown in the accompanying drawings) is to be interpreted as illustrative and not in a limiting sense.

The invention having been described, what is claimed is:

1. Apparatus for monitoring a condition of the body of a human or animal by sensing the breathing movements of said body, comprising in combination:

a resilient pad for supporting a substantial portion of the weight of said body and including a capacitor having a plurality of electrodes including a driven electrode, a receptor electrode and a dielectric layer of elastomer foam separating said electrodes to permit one of said electrodes to move toward and away from the other electrode to cause relatively long term changes in capacitance between the electrodes in response to activity of the body and relatively short term changes in capacitance between the electrodes in response to said breathing movements; and an electronic sensing circuit including (a) means connected to said driven electrode for applying an A.C. drive signal at a frequency that is high enough to be non-hazardous at the voltage levels in use, (b) an amplifier connected to said receptor electrode so that changes in capacitance modulate the output of said amplifier, (c) a demodulator coupled to said amplifier to demodulate the output thereof to produce a fluctuating D.C. signal having fluctuations representative of the changes in capacitance between said electrodes, and (d) high pass filter means coupled to said demodulator for substantially rejecting changes in said D.C. signal representative of relatively long term changes in said capacitance, said sensing circuit being operable to convert said short term capacitance changes to a D.C. output signal representative of said breathing movements.

2. The apparatus of claim 1 wherein said high pass filter means includes an integrator comprising an error amplifier in a closed loop to filter out the effects of said relatively long term changes on the D.C. output signal.

3. The apparatus of claim 1, including audible apnea alarm means coupled to said D.C. output signal to be actuated thereby responsive to cessation of breathing for a selected time period.

4. The apparatus of claim 3 further including a breathing rate measuring circuit and breathing rate alarm means to cause an alarm when breathing rate falls below a preselected level.

5. The apparatus of claim 1, further including a high level comparator for detecting D.C. output signal fluctuations representing body activity of a preselected magnitude considerably greater than those caused by breathing.

6. The apparatus of claim 5, further including means responsive to said comparator for providing a visual indication whenever said activity occurs.

7. The apparatus of claim 1, further including a breath rate measuring circuit coupled through a low level comparator to said sensing circuit and means for visually displaying breath rate connected to said measuring circuit.

* * * * *